United States Patent
Yuen

(10) Patent No.: US 7,338,181 B2
(45) Date of Patent: Mar. 4, 2008

(54) EYE PROTECTING TABLE LAMP HAVING AN AIR PURIFICATION FUNCTION

(76) Inventor: Se Kit Yuen, 6/F, Yau Lee Centre, 45 Hoi Yuen Road, Kwun Tong, Kowloon (HK)

( * ) Notice: Subject to any disclaimer, the term of this patent is extended or adjusted under 35 U.S.C. 154(b) by 79 days.

(21) Appl. No.: 11/125,882

(22) Filed: May 10, 2005

(65) Prior Publication Data

US 2006/0171149 A1    Aug. 3, 2006

(30) Foreign Application Priority Data

Jan. 28, 2005    (CN) .................. 2005 1 0051165

(51) Int. Cl.
  *F21V 33/00* (2006.01)
(52) U.S. Cl. .................. 362/96; 362/253; 96/224; 55/385.1
(58) Field of Classification Search ............... 362/296, 362/2, 33, 576, 162, 166, 196, 231, 247, 362/293, 800, 96, 641, 643, 253, 263, 410; 55/385.1; 250/455.11; 96/224; 422/120, 422/121
See application file for complete search history.

(56) References Cited

U.S. PATENT DOCUMENTS

| | | | |
|---|---|---|---|
| 3,324,387 A * | 6/1967 | Brenner ...................... 324/409 |
| 3,486,308 A * | 12/1969 | Burt ............................. 96/17 |
| 4,439,816 A * | 3/1984 | Litchfield ..................... 362/96 |
| 4,977,489 A * | 12/1990 | Fung ............................ 362/184 |
| 5,217,297 A * | 6/1993 | Yuen ........................... 362/184 |
| 5,256,268 A * | 10/1993 | Goto et al. ................. 204/268 |
| 5,343,114 A * | 8/1994 | Beneking et al. ........... 313/485 |
| 5,349,177 A * | 9/1994 | Thomas et al. ....... 250/214 VT |
| 5,616,172 A * | 4/1997 | Tuckerman et al. ........... 96/16 |
| 5,779,769 A * | 7/1998 | Jiang ............................. 96/55 |
| 6,045,240 A * | 4/2000 | Hochstein ................... 362/294 |
| 6,533,434 B2 * | 3/2003 | Yuen ........................... 362/184 |
| 7,179,425 B2 * | 2/2007 | Yuen ........................... 422/121 |
| 2004/0047772 A1 * | 3/2004 | Kwak .......................... 422/121 |
| 2006/0207138 A1 * | 9/2006 | Yuen ............................. 40/544 |

* cited by examiner

*Primary Examiner*—Alan Cariaso
*Assistant Examiner*—Kevin J. Spinella
(74) *Attorney, Agent, or Firm*—Akerman Senterfitt

(57) ABSTRACT

An air purification apparatus and an illuminating apparatus which provide an eye protecting table lamp that emits gentle light and has an air purification function. The eye protecting table lamp comprises a lamp body unit, a lamp base unit, a focus lamp unit and an air purification unit. The focus lamp unit comprises an illuminant, a cambered reflecting mirror and a light collector. The illuminant has at least one environmentally protective and energy economized LED with minimal heat emission and a long service life. The cambered reflecting mirror is arranged at one side of the illuminant. The light collector is arranged at the side opposite to the reflecting mirror of the illuminant. The air purification unit comprises an air inlet, an extreme ultraviolet emitting device, an air exhaust device, a negative ion generating device and an air outlet.

8 Claims, 9 Drawing Sheets

EYE PROTECTING TABLE LAMP HAVING AN AIR PURIFICATION FUNCTION

FIELD OF THE INVENTION

The present invention relates in general to an air purification apparatus and an illuminating apparatus. More specifically, the present invention relates to an eye protecting table lamp which emits gentle light and has an air purification function.

BACKGROUND OF THE INVENTION

Conventional table lamps have a main body and a fluorescent lamp unit or a focus lamp unit at the other end of the main body. The conventional table lamp has the following disadvantages:

1. The focus lamp unit of the conventional table lamp can give out heat, and thus the focus lamp can burn a user's hand when the user adjusts the illumination angle.
2. The fluorescent lamp unit or focus lamp unit of the conventional table lamp can give off high-intensity light, which can damage the eyes of a user or cause the user to feel bad when the user is reading or working under such high-intensity light for a long time.
3. The conventional table lamp does not have an apparatus and a function for sterilization, disinfection and fresh air generation.

SUMMARY OF THE INVENTION

In view of the above disadvantages in the prior art, the object of the present invention is to provide an eye protecting table lamp which emits gentle light and has an air purification function.

In order to achieve the above object, an eye protecting table lamp having an air purification function comprises a lamp body unit, a lamp base unit, a focus lamp unit and an air purification unit. The focus lamp unit comprises an illuminant, a curved reflecting mirror and a light collector. The illuminant has one or more than one environmentally protective and energy economized LED with minimal heat emission and has a long service life. The curved reflecting mirror is arranged at one side of the illuminant for uniformly reflecting light from the illuminant. The light collector is transparent and is arranged at the side opposite to the reflecting mirror of the illuminant for causing the light from the illuminant to be emitted in a convergent manner. Thus, through the precise coupling between the light collector and the curved reflecting mirror, the light source is improved in light intensity and is uniformly collected as a beam of gentle light which is good for the eye protection.

Further, the upper end of the lamp body unit is coupled by a pivot to an end of the focus lamp unit, and the lower end of the lamp body unit is fixedly connected to the air purification unit whose lower end is fixedly connected to the lamp base unit. Accordingly, the focus lamp unit can rotate round the pivot point with respect to the lamp body unit at an angle ranging from 0 to 180 degrees, thus to provide an optimum illuminating angle for a user of the lamp.

Further, the air purification unit comprises an air inlet, an extreme ultraviolet emitting device, an air exhaust device, a negative ion generating device and an air outlet which are connected in this turn. Because both the extreme ultraviolet emitting device and the negative ion generating device are used at the same time, the air purification unit has multiple purification functions which could kill bacteria, virus and mildew in the air and provide fresh air having an abundance of negative ions.

The extreme ultraviolet emitting device comprises an air aggregation unit, an extreme ultraviolet radial tube arranged at the center of the air aggregation unit, an air aggregation wall for aggregating the air and making it flow through the extreme ultraviolet radial tube, a dust removal device arranged at the air inlet end of the air aggregation unit, and an air aggregation sash which is arranged at the air outlet end of the air aggregation unit for facilitating the entry of air and making the air arrive at the air outlet through the air aggregation unit. Because the extreme ultraviolet radial tube is provided and the air collectively passes through the extreme ultraviolet radial tube by the air aggregation structure, the bacteria, virus and mildew in the air could be effectively killed.

Further, shielding walls are provided respectively at the air inlet end and the air outlet end to prevent the ultraviolet which may hurt the user from radiating outward.

Further, the negative ion generating device comprises a cathode high voltage fiber thread which is arranged in the air outlet.

Further, the lamp base unit is provided with a switch for turning on or off the power of the focus lamp unit through contacting with or release from the focus lamp unit.

Compared with the prior art, the above technical scheme of the present invention has the following advantages:

1. Gentle light is emitted, by which the eyes of a user will not be damaged and the user will not feel tired even reading for a long time, thus a good eye protecting effect is obtained.
2. The defection that a user's hand is burned by the focus lamp unit is removed.
3. Sterilizing the indoor air and providing fresh air in abundance of negative ion.

Embodiments of the present invention will be described below with reference to the drawings.

DETAILED DESCRIPTION OF THE PREFERRED EMBODIMENT

Figure 1:
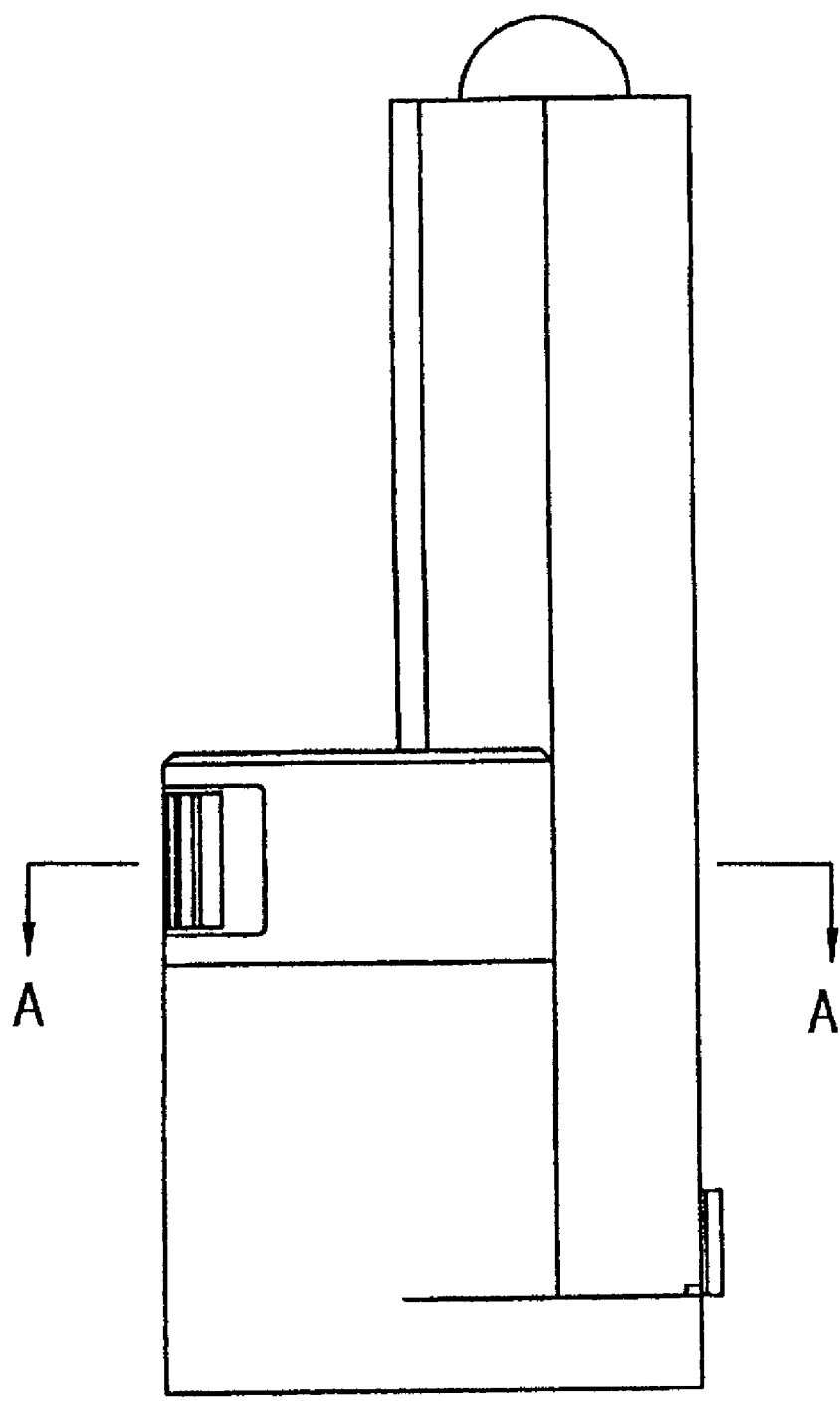
FIG. 1 is a left side view of an eye protecting table lamp having an air purification function in an off state according to the present invention.

Referring to FIGS. 1-11, an eye protecting table lamp having an air purification function according to the present invention comprises a lamp body unit 1 which generally has a rectangular parallelepiped structure, an air purification unit 2, a lamp base unit 23 and a focus lamp unit 30. The lower end of the lamp body unit 1 is fixedly coupled to the air purification unit 2 comprising a cylindrical frame 3 and an air exhaust sash 4 which is fixed to the forward end of the frame 3 and through which the ionized air is exhausted.

Figure 2:
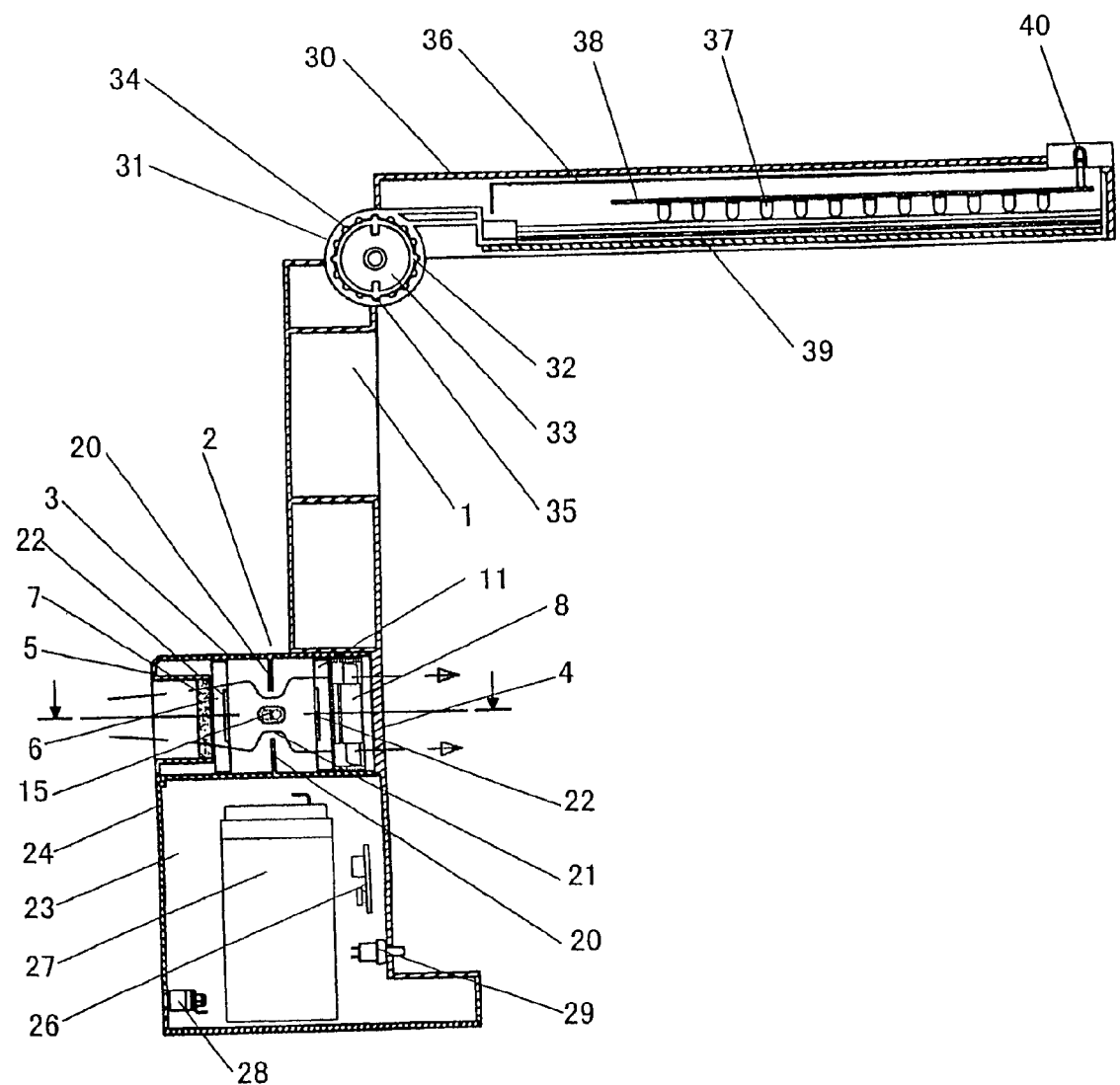
FIG. 2 is a left side cross section view of the eye protecting table lamp having an air purification function in a opened state according to the present invention.
Figure 3:
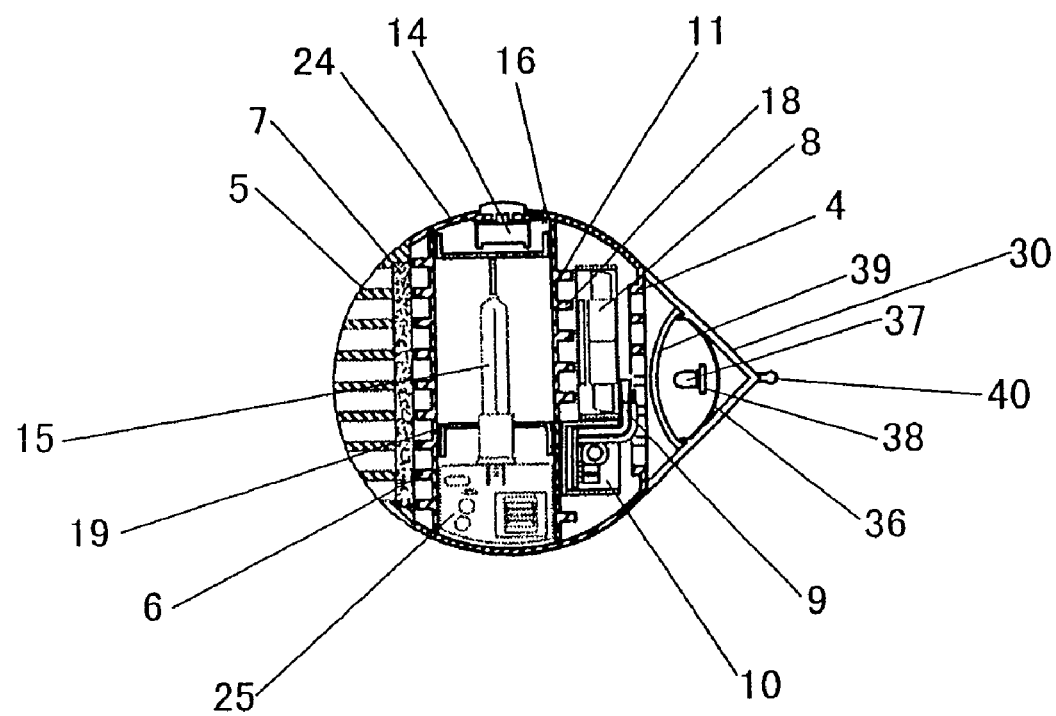
FIG. 3 is a A-A cross section view of the eye protecting table lamp having an air purification function shown in FIG. 1.
Figure 4:
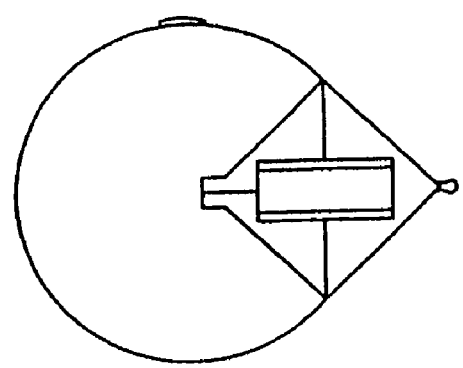
FIG. 4 is a top view of the eye protecting table lamp having an air purification function shown in FIG. 1.
Figure 5:
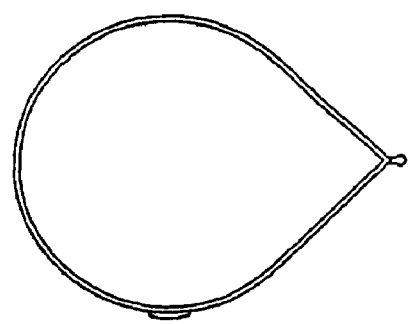
FIG. 5 is a bottom view of the eye protecting table lamp having an air purification function shown in FIG. 1.
Figure 6:
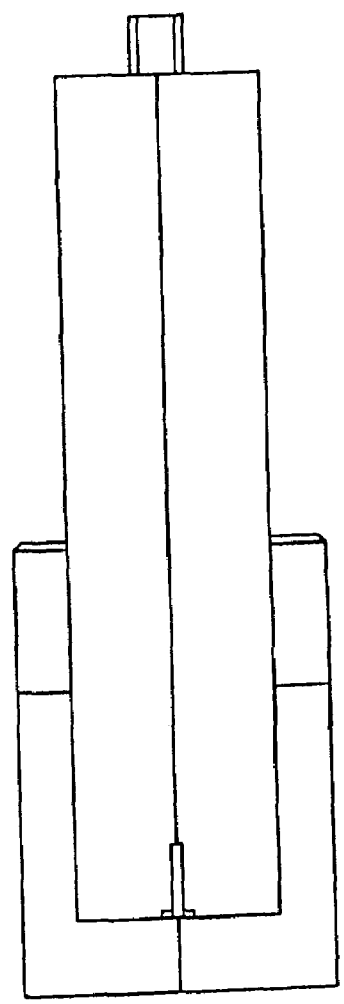
FIG. 6 is a front view of the eye protecting table lamp having an air purification function shown in FIG. 1.
Figure 7:
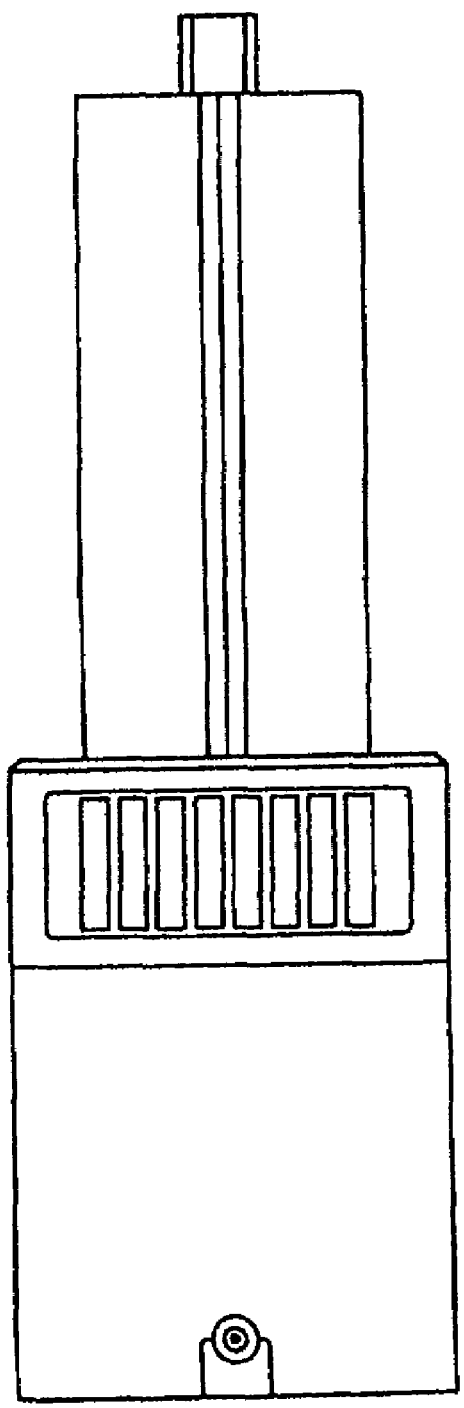
FIG. 7 is a back view of the eye protecting table lamp having an air purification function shown in FIG. 1.
Figure 8:
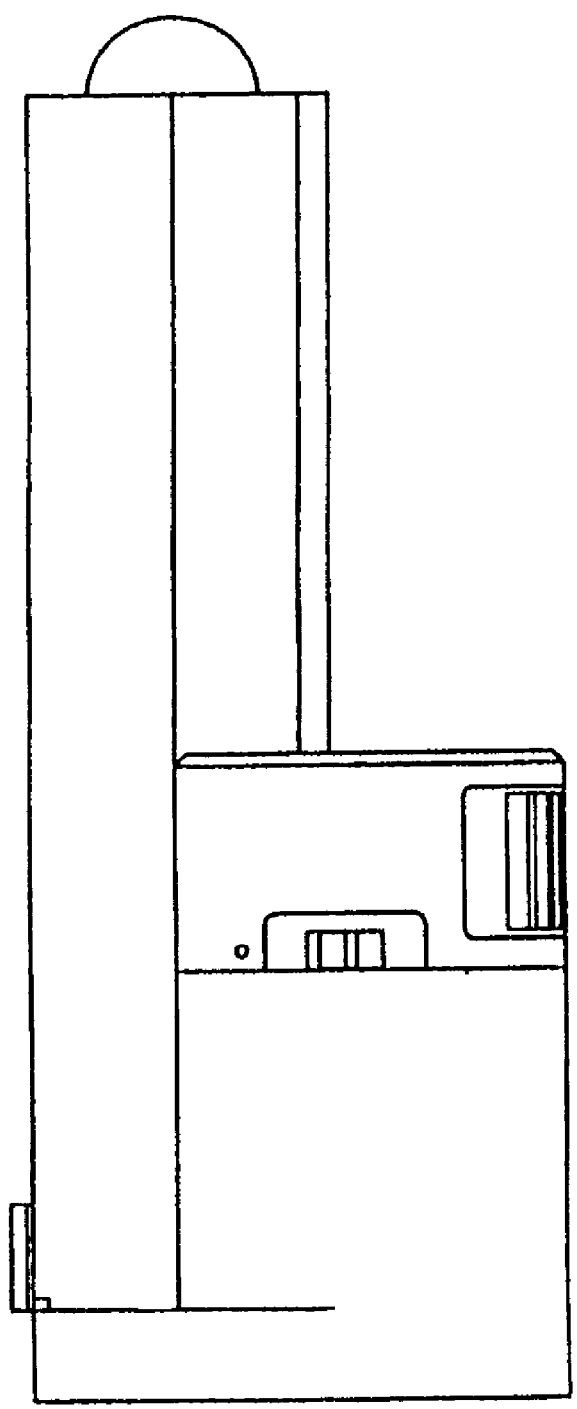
FIG. 8 is a right side view of the eye protecting table lamp having an air purification function shown in FIG. 1.
Figure 9:
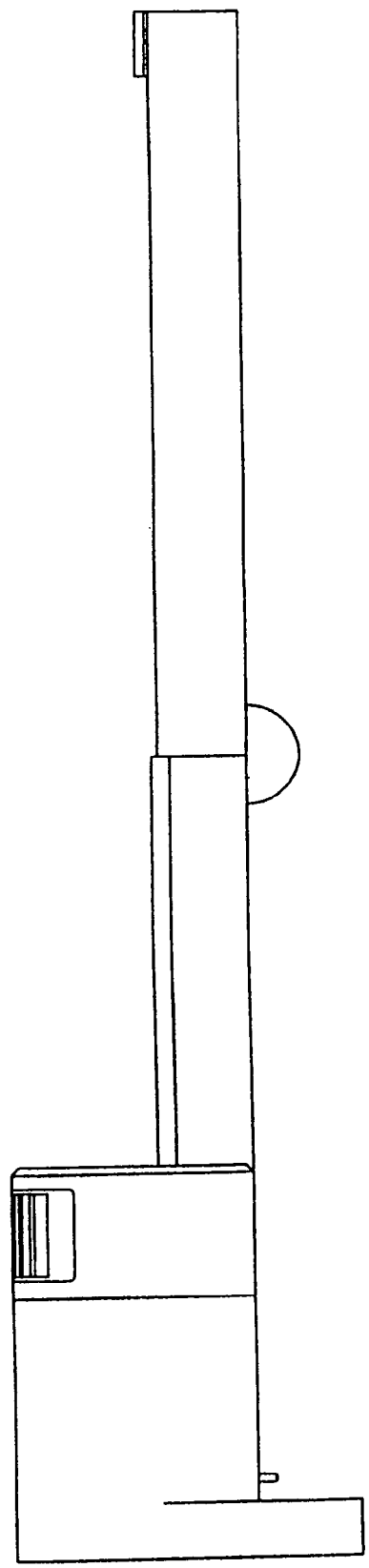
FIG. 9 is a view of the eye protecting table lamp having an air purification function shown in FIG. 1 in another opened state.
Figure 10:
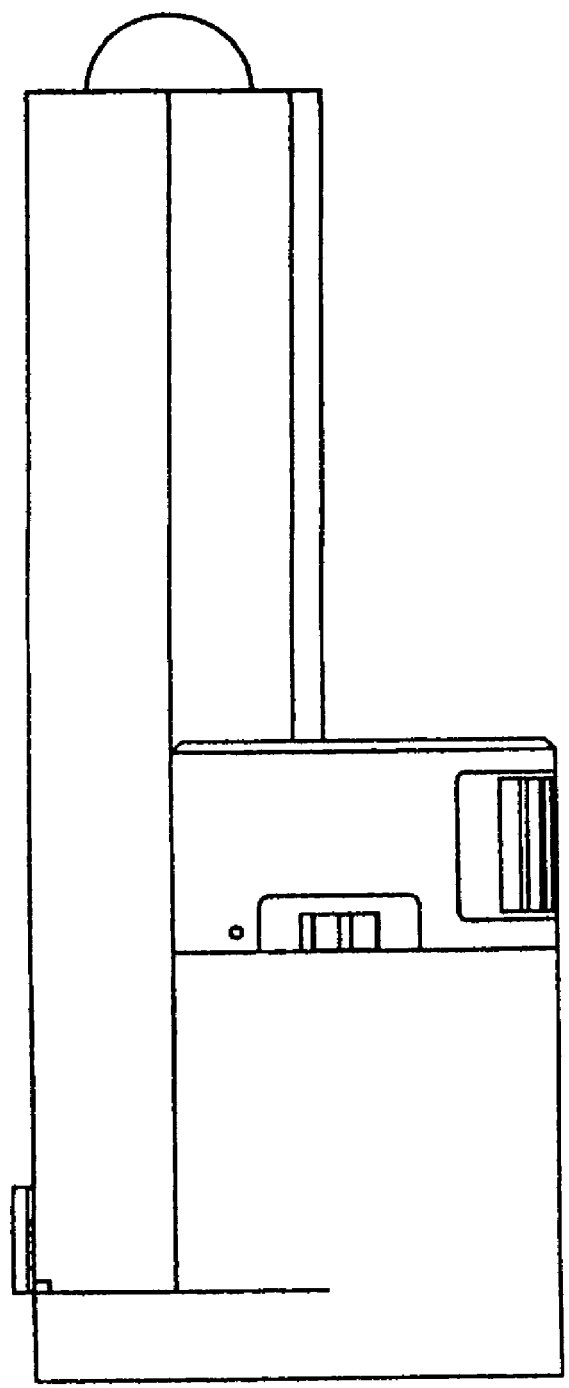
FIG. 10 is a perspective view of the eye protecting table lamp having an air purification function shown in FIG. 1 in a off state.
Figure 11:
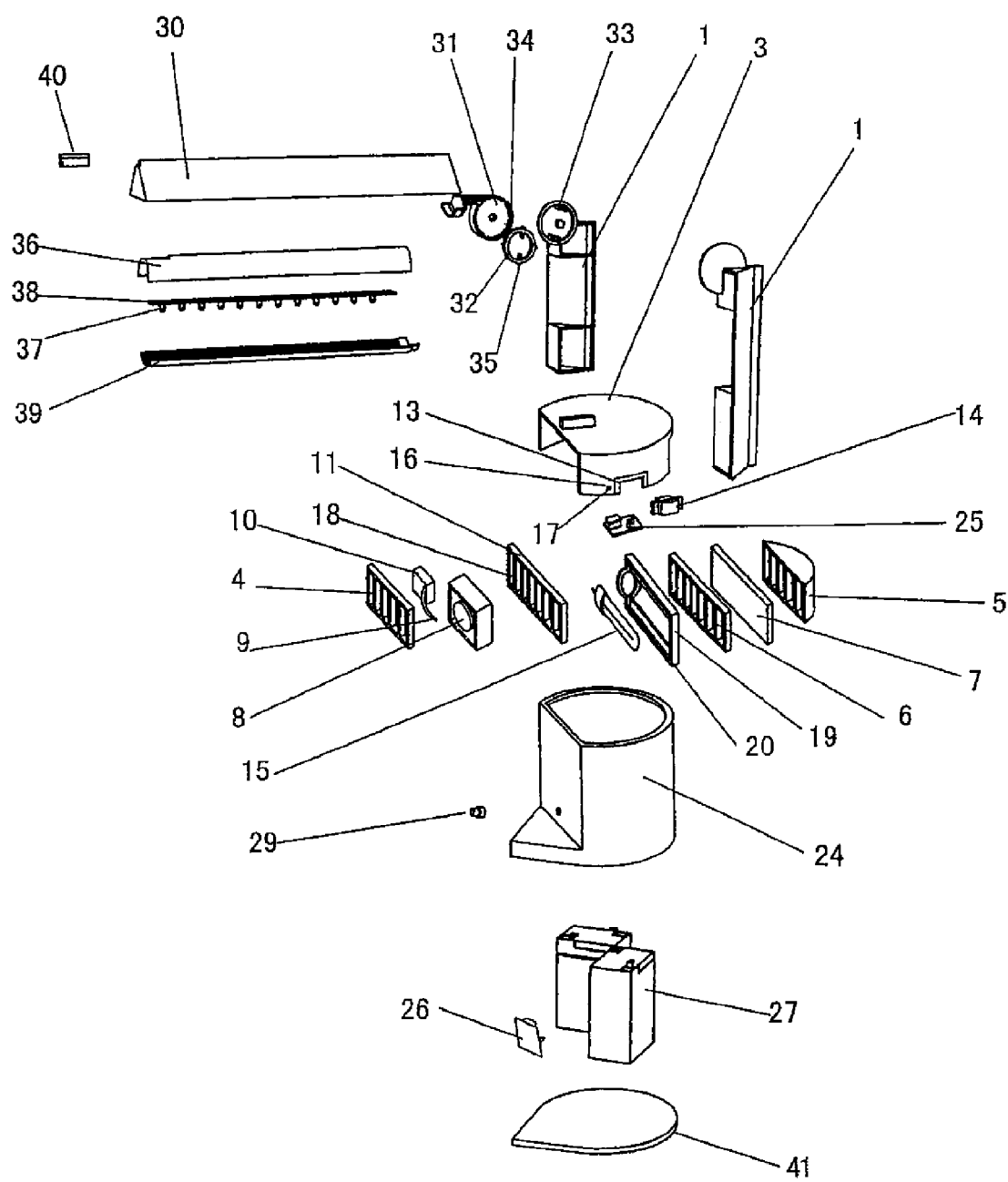
FIG. 11 is an exploded view of the eye protecting table lamp having an air purification function shown in FIG. 1.

The particular structure of the eye protecting table lamp having an air purification function is shown in FIGS. 2 and 3. The rear end of the frame 3 is provided with an air intake 5 which provides a fixed dust insulation shelf 6 and a dust insulation screen 7. An exhaust fan 8 is adjacently provided on the inner surface of the air exhaust sash 4 to work as an air exhaust device. A carbonized fiber thread 9 which can generate ionized air under cathode high voltage is fixed at the center of the back surface of The air exhaust sash 4. A space for accommodating a fixed power supply electronic generator 10 is provided beside the exhaust fan 8, and an air aggregation sash 11 is arranged at the rear end of the exhaust fan 8. A rectangular hole site 13 is provided on the side surface of the frame 3 to fix a change-over switch 14 which controls The exhaust fan 8, an extreme ultraviolet radial tube 15 and The carbonized fiber thread 9. The extreme ultraviolet radial tube 15 does not need to be replace and also does not give out much heat and is environmentally protective and energy economized. A hole site 16 is provided on the plane beside the change-over switch 14 for fixing light-emitting diode 17 emitting light of different colors which serves as a function indicator.

When the air purification unit 2 of the eye protecting table lamp having an air purification function is activated, the air containing bacteria, virus and mildew is drawn in by the exhaust fan 8 and enters into the air aggregation sash 11 in the frame 3 through the dust insulation screen 7. The air aggregation sash 11 has a plurality of strip grids 18 to facilitate the entry of the air and enable the air to arrive at the air exhaust sash 4 through an air aggregation unit 19. And the extreme ultraviolet radial tube 15 is arranged at the center of the air aggregation unit 19. In other words, the air containing bacteria, virus and mildew moves and enters into an air aggregation wall 20 at both sides of the air aggregation unit 19, and then into an air inlet 21 between the extreme ultraviolet radial tube 15 and the air aggregation wall 20. When the air containing bacteria, virus and mildew enters into the air inlet 21, the extreme ultraviolet radial tube 15 emits extreme ultraviolet having a wavelength of 253.7 nm which could effectively killed the bacteria, virus and mildew in the air. Then the purified air is exhausted to the air exhaust sash 4 by the exhaust fan 8. And during this course, a negative ion purification process is performed by the cathode high voltage carbonized fiber thread 9. Accordingly, fresh air in abundance of negative ion is exhausted from the air exhaust sash 4, by which the indoor air quality is improved.

In addition, two kinds of alternate operation manners could be adopted when the air is drawn in the air purification unit by the exhaust fan. In the first operation manner, an intermittent cathode high voltage (about 3 to 4 minutes) is outputted and electrically discharged via the carbonized fiber thread, and negative ion is generated by the ionization of air and is exhausted by the exhaust fan. In the second operation manner, the extreme ultraviolet radial tube 15 is intermittently activated to kill the bacteria, virus and mildew in the air. The above two manners could be alternated or combined, thus to meet the requirements of various purification.

Shielding walls 22 are provided in front of and behind the air aggregation unit 19 to prevent the extreme ultraviolet from radiating out of the frame 3, thus to protect the user's eyes.

The circuit principle of the air purification unit 2 is described as follows: the commercial power from the power supply is supplied to a negative ion high voltage generating circuit via a change-over switch for providing a negative high voltage output; the voltage from the power supply is supplied to the exhaust fan 8 additionally via a full wave rectifier circuit and a speed control activation circuit 25, and through a DC/AC convert circuit to activate the full wave rectifier circuit of the extreme ultraviolet radial tube 15; the other route of power is supplied to an automatic cycle control circuit of the activation circuit for the negative ion generating circuit/extreme ultraviolet radial tube 15 via a voltage stabilizing circuit, thus to control the negative ion generating unit and the extreme ultraviolet radial tube 15 to operate alternatively.

The negative ion generated by the negative ion generating unit can accelerate biochemical action (increase the amount of breathed in negative ion) and constrain the secreting of hormones which can lead to depression and fatigue.

The air purification unit 2 of the eye protecting table lamp having an air purification function according to the present invention is connected at its lower end to a lamp base unit 23 which has a cylindrical base body 24, a power supply convert circuit 26, a rechargeable battery 27, an external power plug 28 and an automatic change-over switch 29.

The focus lamp unit 30 is fixedly coupled at its upper end to an articulated coupler 31. It also comprises a flexible annular fixed guide 32 which is fastened in the coupling shaft 33 at the upper end of the lamp body unit 1. The coupling shaft 33 of the lamp body unit 1 and the annular fixed guide 32 are rotatably inserted into gear teeth 34 of the articulated coupler 31. At least one of engaging teeth 35 is projected from the exterior circumferential surface of the annular fixed guide 32 to be selectively engaged with the plurality of gear teeth 34 in order that the rotation position of the focus lamp unit 30 relative to the lamp body unit 1 is fixed. The gear teeth 34 are uniformly formed on the exterior circumferential surface of the annular fixed guide 32. The articulated coupler 31 is rotatably coupled to the focus lamp unit 30 and is coupled to the coupling shaft 33 of the lamp body unit 1, thus to rotatably adjust the fold angle between the lamp body unit 1 and the focus lamp unit 30. Therefore, the illumination angle of the focus lamp unit 30 could be adjusted with respect to the lamp body unit 1.

The focus lamp unit 30 generally has a rectangular parallelepiped structure. It comprises a curved reflecting mirror 36 which is provided at its lower end with a group of (at least one) LED(s) 37 arranged on the circuit board 38. At the lower end of the group LEDs 37 is a light collector 39 which is made of transparent material. A power indicator 40 is provided at the tail end of the focus lamp unit 30. Light emitted from the LED 37 as a light source is converged by the transparent light collector 39 and is reflected uniformly by the curved reflecting mirror 36 provided at the other end of the LED 37 to form an illuminant. In virtue of the precise coupling between the transparent light collector 39 and the curved reflecting mirror 36, light intensity of the light source is improved and the light is uniformly converged into a beam of gentle light under which the user's eyes will not be hurt or feel tired even if the lamp is used for reading for a long time. The table lamp of the present invention is particularly beneficial to children in that it can protect their eyes when they do homework using the lamp.

The lamp base unit 23 includes a planar support 41 for supporting the lamp body unit 1 of the eye protecting table lamp having an air purification function. The other end of the lamp body unit 1 is movably coupled to the focus lamp unit 30 which could move between a first position shown in FIG. 1 and a second position shown in FIG. 9. In the first position, the focus lamp unit 30 is parallel to the lamp body unit 1. And in the second position, the focus lamp unit 30 is in alignment with the lamp body unit 1 and could rotate about a pivotal hinge to move to any position within an arc of 180 degrees. The automatic change-over switch 29 of the lamp base unit 23 is in a closed position when the focus lamp unit 30 is in the first position. And when the focus lamp unit 30 moves away from the first position, the automatic change-over switch 29 of the lamp base unit 23 will activate the power supply convert circuit 26, by which the curved reflecting mirror 36 of the focus lamp unit 30 as a light source is uniformly reflected to form an illuminant. Accordingly, the lamp base unit 23 provides a planar support for the eye protecting table lamp having an air purification function.

The eye protecting table lamp having an air purification function may use commercial power, vehicle power or an internal rechargeable battery as a power source. And the rechargeable battery could be recharged when a commercial power is applied, thus the inner rechargeable battery will automatically activate a circuit to turn on the light source of the LED eye protecting table lamp. In other words, the eye protecting table lamp having an air purification function could also function as an emergency light. The eye protecting table lamp having an air purification function according to the present invention has a service life of 100,000 hours and has a good security, without being influenced by weather. The eye protecting table lamp having an air purification function according to the present invention could continuously work for 32 hours after one time of electrical charging.

The eye protecting table lamp having an air purification function according to the present invention also serves as a light shield when a computer is used in the dark. Thus light radiation and high frequency flash is avoided from directly stimulating the eyes, which enables the user to concentrate more and improve work efficiency.

What is claimed is:

1. An eye protecting table lamp having an air purification function, comprising:
    a lamp body unit;
    a lamp base unit;
    a focus lamp unit; and
    an air purification unit,
    wherein the focus lamp unit comprises an illuminant having at least one environmentally protective and energy economized LED with minimal heat emission; a curved reflecting mirror which is arranged at one side of the illuminant for uniformly reflecting light from the illuminant; and a transparent light collector which is arranged at the side opposite to the reflecting mirror of the illuminant for causing the light from the illuminant to be emitted in a convergent manner,
    wherein the air purification unit comprises an air inlet, an extreme ultraviolet emitting device, an air exhaust device, a negative ion generating device and an air outlet which are connected in this turn, and
    wherein the negative ion generating device comprises a cathode high voltage fiber thread which is arranged in the air outlet.

2. The eye protecting table lamp having an air purification function according to claim 1, wherein the at least one LED is provided on a circuit board.

3. The eye protecting table lamp having an air purification function according to claim 1, wherein the upper end of the lamp body unit is coupled by a pivot to an end of the focus lamp unit, and the lower end of the lamp body unit is fixedly connected to the air purification unit whose lower end is fixedly connected to the lamp base unit.

4. The eye protecting table lamp having an air purification function according to claim 3, wherein the focus lamp is movably coupled to the lamp body unit by an articulated coupler, a flexible annular fixed guide and coupling shaft, wherein the articulated coupler is provided on the focus lamp unit and has gear teeth at its interior circumference, and the articulated coupler is provided at its exterior circumference wit one or more than one engaging teeth which are engaged with the gear teeth, the coupling shaft being provided at the upper end of the lamp body unit and being rotatably inserted into the articulated coupler together with the annular fixed guide.

5. The eye protecting table lamp having an air purification function according to claim 3, wherein the lamp base unit is provided with a switch for turning on or off the power of the focus lamp unit through contacting wit or release from the focus lamp unit.

6. The eye protecting table lamp having an air purification function according to claim 1, wherein the extreme ultraviolet emitting device comprises an air aggregation unit, an extreme ultraviolet radial tube arranged at the center of the air aggregation unit, an air aggregation wall for aggregating the air and making it flow through the extreme ultraviolet radial tube, a dust removal device arranged at the air inlet end of the air aggregation unit, and an air aggregation sash which is arranged at the air outlet end of the air aggregation unit for facilitating the entry of air and making the air arrive at the air outlet through the air aggregation unit.

7. The eye protecting table lamp having an air purification function according to claim 6, wherein shielding walls are provided respectively at the air inlet end and the air outlet end to prevent the ultraviolet which may hurt the user from radiating outward.

8. The eye protecting table lamp having an air purification function according to claim 1, wherein the extreme ultraviolet emitting device generates an extreme ultraviolet having a wavelength of 253 nm, and the output of the cathode high voltage generated by the negative ion generating device is 4.5-8.5 kv.

* * * * *